(12) United States Patent
Davis

(10) Patent No.: US 9,936,704 B2
(45) Date of Patent: *Apr. 10, 2018

(54) ANTIMICROBIAL COLLOIDAL SILVER PRODUCTS AND METHOD OF MAKING SAME

(71) Applicant: Eco Product Group LLC, Pittsburgh, PA (US)

(72) Inventor: Thomas P. Davis, Wexford, PA (US)

(*) Notice: Subject to any disclaimer, the term of this patent is extended or adjusted under 35 U.S.C. 154(b) by 47 days.

This patent is subject to a terminal disclaimer.

(21) Appl. No.: 14/583,975

(22) Filed: Dec. 29, 2014

(65) Prior Publication Data

US 2015/0110896 A1    Apr. 23, 2015

Related U.S. Application Data

(63) Continuation of application No. 13/151,937, filed on Jun. 2, 2011, now Pat. No. 8,920,850.

(60) Provisional application No. 61/350,626, filed on Jun. 2, 2010.

(51) Int. Cl.
| | | |
|---|---|---|
| *A01N 25/34* | (2006.01) |
| *A01N 59/16* | (2006.01) |
| *B29C 39/00* | (2006.01) |
| *B29C 39/02* | (2006.01) |
| *B65D 37/00* | (2006.01) |
| *A63B 21/00* | (2006.01) |
| *B29L 7/00* | (2006.01) |
| *B29L 23/00* | (2006.01) |

(52) U.S. Cl.
CPC .......... *A01N 59/16* (2013.01); *A63B 21/4037* (2015.10); *B29C 39/003* (2013.01); *B29C 39/026* (2013.01); *B65D 37/00* (2013.01); B29L 2007/001 (2013.01); B29L 2023/003 (2013.01); Y10T 428/24479 (2015.01); Y10T 428/2976 (2015.01)

(58) Field of Classification Search
CPC .................. B29L 2007/001; B29L 2023/003
See application file for complete search history.

(56) References Cited

U.S. PATENT DOCUMENTS 8,920,850 B2 * 12/2014 Davis .................. A01N 59/16
424/1.25

* cited by examiner

*Primary Examiner* — Ali Soroush
(74) *Attorney, Agent, or Firm* — David G. Oberdick

(57) ABSTRACT

Gelatinous materials combined with the Colloidal Silver additive to formulate an antimicrobial product having cushioning properties. Embodiments of the present invention can include gelatinous materials selected from a group consisting of thermosetting polymer, Styrene-Ethylene-Butadiene-Styrene polymer (SEBS), Thermoplastic Elastomer (TPE), and Polyurethane (PU) gelatin with and without a raised geometry on an outer surface.

2 Claims, 19 Drawing Sheets

ANTIMICROBIAL COLLOIDAL SILVER PRODUCTS AND METHOD OF MAKING SAME

CROSS-REFERENCE TO RELATED APPLICATIONS

The present invention is a Continuation Application of U.S. Non-Provisional application Ser. No. 13/151,937, entitled "ANTIMICROBIAL COLLOIDAL SILVER PRODUCTS AND METHOD OF MAKING SAME" filed Jun. 2, 2011, which claims benefit of U.S. Provisional Application Ser. No. 61/350,626, entitled ANTIMICROBIAL COLLOIDAL SILVER PRODUCTS AND METHOD OF MAKING SAME, filed on Jun. 2, 2010, all are incorporated herein by reference.

FIELD OF THE INVENTION

The present invention is related generally to the field of antimicrobial products, and in particular antimicrobial colloidal silver products.

BACKGROUND OF THE INVENTION

Traditionally, TPE Gels (Thermoplastic Elastomers) are developed by the hydrogenation of tri-block co-polymers of styrene and butadene. The present invention formulation allows for the glass transition of its rubber block below-50° C. thus maintaining its rubbery properties. This material content gel is made up of visco-elastic properties that are transformed into a gelatinous mass. The Tri-Block Co-Polymer, for example, uses mineral oil as a plasticizer. The Styrene-Ethylene-Butadiene-Styrene polymer (SEBS) description then becomes styrene and ethylene-butylene, and mineral oil is used for the modification of viscosity, and flexibility and strength of blends. The major applications for this type of gel have been for sealants, adhesives, coatings, footwear, athletic equipment, and other cushioning parts.

SUMMARY OF THE INVENTION

Generally, the present invention includes gelatinous materials combined with the Colloidal Silver additive to formulate an antimicrobial product having cushioning properties. Embodiments of the present invention can include gelatinous materials selected from a group consisting of thermosetting polymer, Styrene-Ethylene-Butadiene-Styrene polymer (SEBS), Thermoplastic Elastomer (TPE), and Polyurethane (PU) gelatin with and without a raised geometry on an outer surface.

For a better understanding of the present invention, together with other and further objects thereof, reference is made to the accompanying drawings and detailed description.

BRIEF DESCRIPTION OF THE DRAWINGS

The present invention is illustratively shown and described in reference to the accompanying drawings, in which.

DETAILED DESCRIPTION OF THE INVENTION

As used herein in the specification and claims, including as used in the examples and unless otherwise expressly specified, all numbers may be read as if prefaced by the word "about", even if the term does not expressly appear. Also, any numerical range recited herein is intended to include all sub-ranges subsumed therein.

The phrase "cross-linked network" means the one polymer chain is linked or bonded to another polymer chain.

The phrase "monolithic structure" means a solid, single part and not an assembly of two or more components.

The phrase "comprehensively suspended colloidal silver" means silver particulates are suspended evenly throughout the gel material or suspended unevenly but along a target surface, such as the outer surface, of the gel material, both of which provides sufficient antimicrobial protection for its intended purpose.

One embodiment of the present invention comprises a gelatinous material with a colloidal silver additive suspended substantially evenly within the gelatin material. The gelatinous material can either be a thermosetting polymer, Styrene-Ethylene-Butadiene-Styrene polymer (SEBS), Thermoplastic Elastomer (TPE), or Polyurethane (PU) gelatin. The thermo-reversible solid material is composed of a liquid organic phased entrapped in a three-dimensionally cross-linked network. The solubility of the liquid organic can add elasticity to a product creating a jelly-like substance or gelatinous material. The combination of organic material plus SEBS material creates a thermoplastic elastomer. The polymers will be used in a final form in hardness and softness ranging from 0 to 40 on the shore A scale and harder consistencies on the Shore DD Scale from 0 to 80. The range of the TPE Gels will be from 0 to 40 on the 00 scale of measurement (Durometer). For the purpose of illustration, one embodiment of the gelatinous material is:

Substance A: Polymeric Methylene diphenyl di-isocyanate (MDI) 100%;

Substance B: 265 Molecular weight (Mw) polyether triol 100%;

Ratio A:B about 1:1; and

Shore D about 80.

Figure 15:
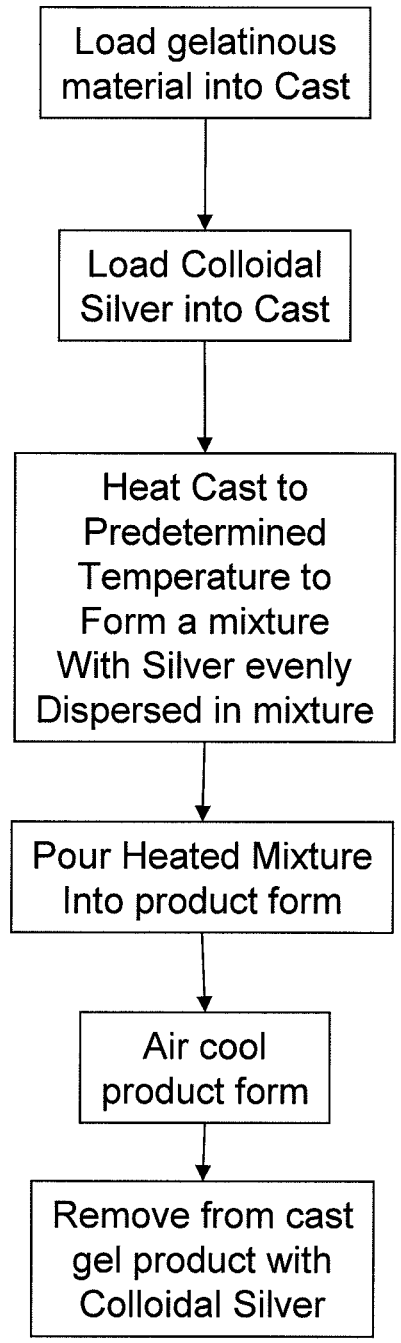
FIG. 15 is a flow diagram of the manufacturing process.

One method of preparing the present invention, illustrated in FIG. 15, treats a batch of gelatinous material with a suspended Colloidal Silver additive (for example, SmartSilver™ manufactured by NanoHorizons, Inc.), which when loaded will totally penetrate all areas of each substance and provide a green tinge to the color of the gelatinous material or plastic. A green tinge indicates that the silver additive has dispersed evenly in the material. The Colloidal Silver additive will inhibit the spread of over 650 bacteria strains including staph, Methicillin-resistant *Staphylococcus aureus* (MRSA), *E-Coli* and other less well-known strains.

The prefabricated forms are allowed to set-up or air dry with very little pressure in order to derive the cast parts. The process of pouring the gelatinous material at ambient pressure conditions (1 atmosphere) and air casting is contrary to the conventional method of injection molding the gelatinous material under pressure conditions (above 1 atmosphere).

The next step is to mix the Colloidal silver additive in liquid or powder form into the gelatinous material in the cast prior to the first melt stage. Thusly, the colloidal silver is dispersed into part A and B of the A/B gelatinous material.

As stated above, the gelatinous material and Colloidal silver additive are combined to form a gelatinous mixture through a cast/pouring method. The gelatinous mixture in the cast is heated to a predetermined temperature ranging from about 300 degrees F. to up to the boiling point of the gelatinous material, and poured into prefabricated forms that are in the shape of the products to be derived from the casting of the materials.

In one embodiment of the gelatinous material in pellet form, the Colloidal silver additive is suspended simultaneously with the pellets, heated about 300° F., and poured into the prefabricated forms under ambient pressures conditions (1 atmosphere) and not under pressure (above 1 atmosphere) as.

The resultant material derived from either process will be a gelatinous material with comprehensively suspended colloidal silver throughout the gelatinous material. The final shape of the gelatinous material can take many forms, examples of which are provided below. However, the scope of the present invention is not to be limited to the examples provided herein.

Figure 1:
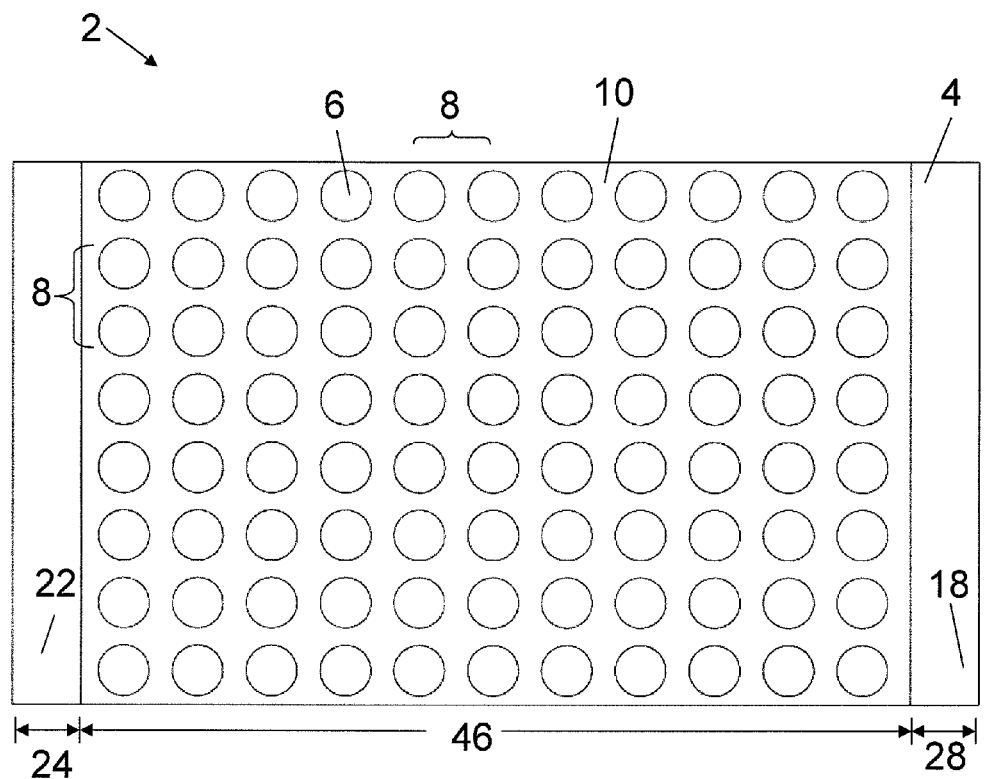
FIG. 1 is a top view of an exemplary embodiment of a flat mat of the present invention, which has a top surface with a plurality semi-circular projections arranged in rows on a flat surface.
Figure 2:
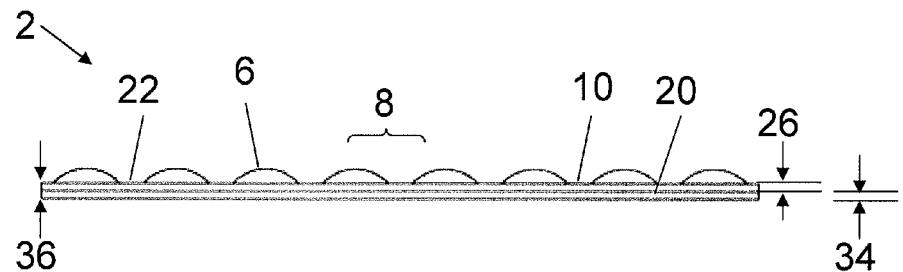
FIG. 2 is a end view of the exercise pad of FIG. 1.
Figure 3:
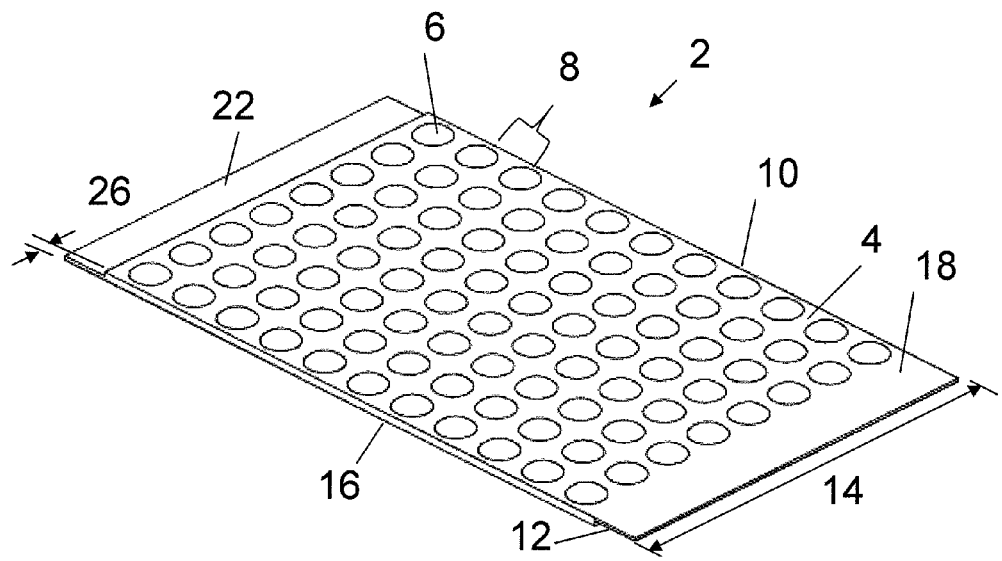
FIGS. 3 and 4 are perspective views of an embodiment of the flat mat of FIG. 1.
Figure 4:
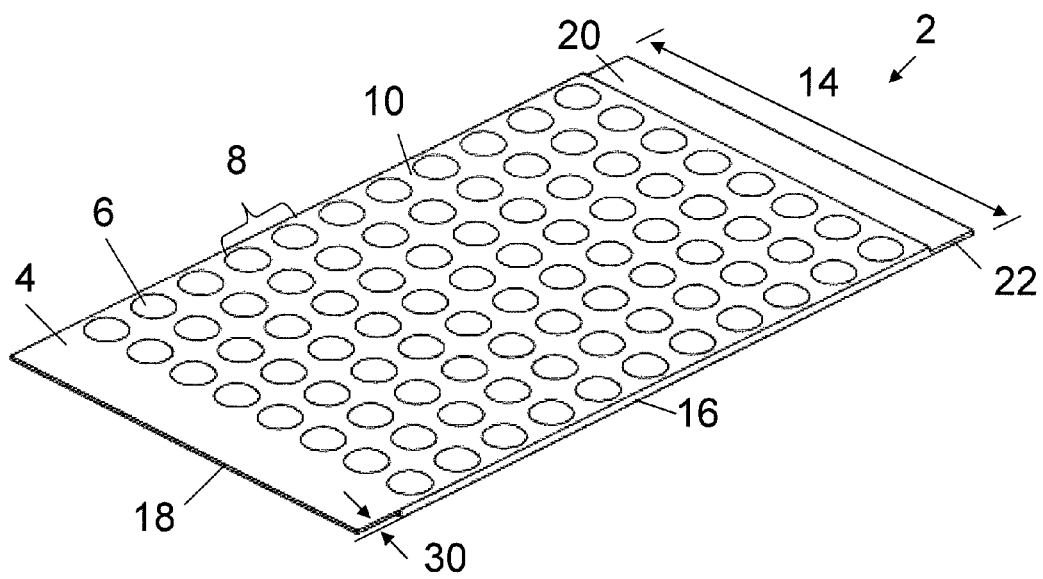
Figure 5:
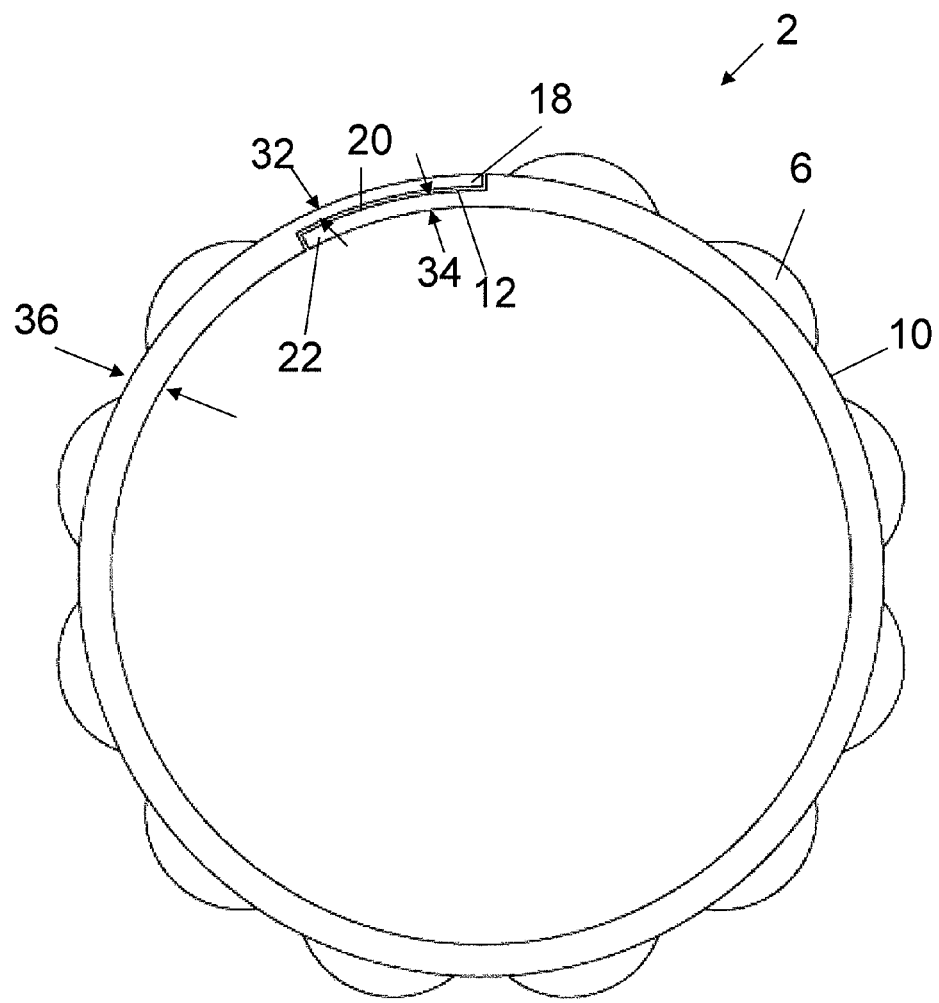
FIG. 5 is an end view of the flat mat of the embodiment of FIG. 1 rolled with ends attached thereto.

One embodiment of the present invention is illustrated in FIGS. 1-8 illustrates a flat mat 2 and examples of its possible adaptable configurations. FIG. 1 is a top view of an exemplary embodiment being a flat mat 2 of the present invention; which has a top surface 4 with a plurality of semi-circular projections 6 arranged in rows 8 on a flat surface 10. FIG. 2 is an end view of the flat mat 2 of FIG. 1. FIGS. 3 and 4 are perspective views of an embodiment of flat mat 2 of FIG. 1 illustrating cutout 12 along width 14 of bottom surface 16 at end 18 and cutout 20 along width 14 of top surface 10 at opposing end 22. FIGS. 1 and 2 illustrate top surface cutout 20 having length 24 and depth 26 substantially the same dimensions as bottom surface cutout 12 with length 28 and depth 30, respectively, such that when flat mat 2 is rolled into a substantially circular form, as shown in FIG. 5, end 18 and opposing end 20 are received into top surface cutout 20 and bottom surface cutout 12, respectively. Another acceptable embodiment of ends 18, 22 is any combination of cutout depths 26, 30 or end thicknesses 32, 34 with a sum total thickness approximately equivalent to flat mat thickness 36. Ends 18, 22 are removably attachable by any suitable attachment mechanism such as hook/loop, adhesive, male/female snaps, and clamps.

Figure 19A:
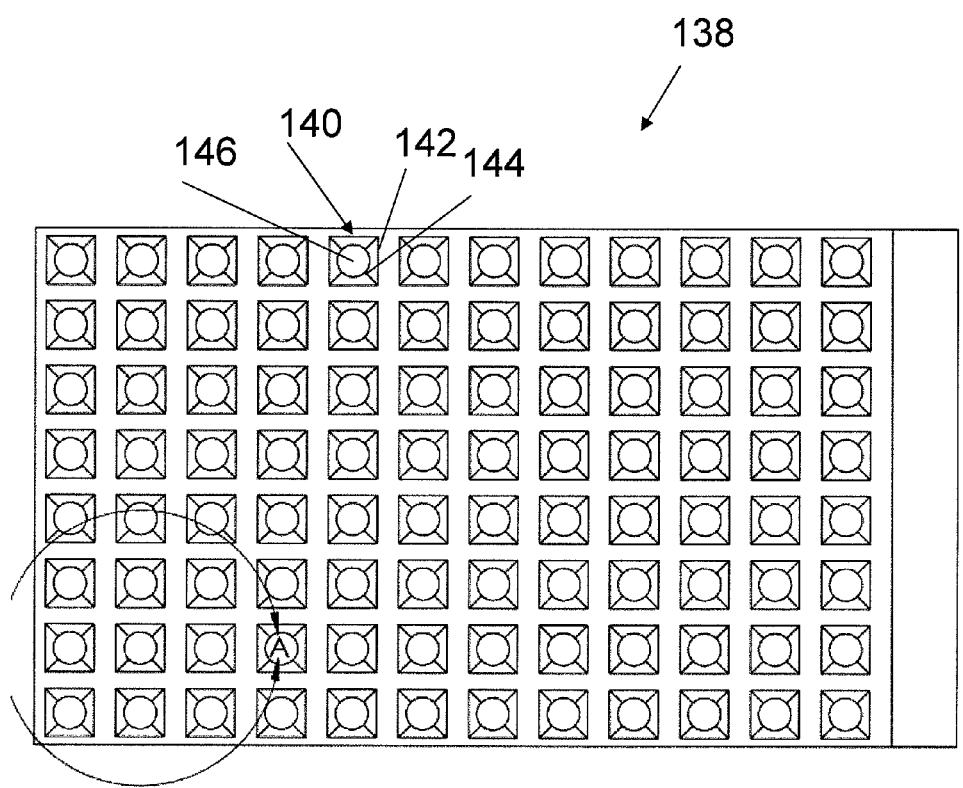
FIG. 19A is a top view of an alternative embodiment of a flat mat illustrating an alternative projection with a square base section having side that rise to form a semi-circular top section.
Figure 19B:
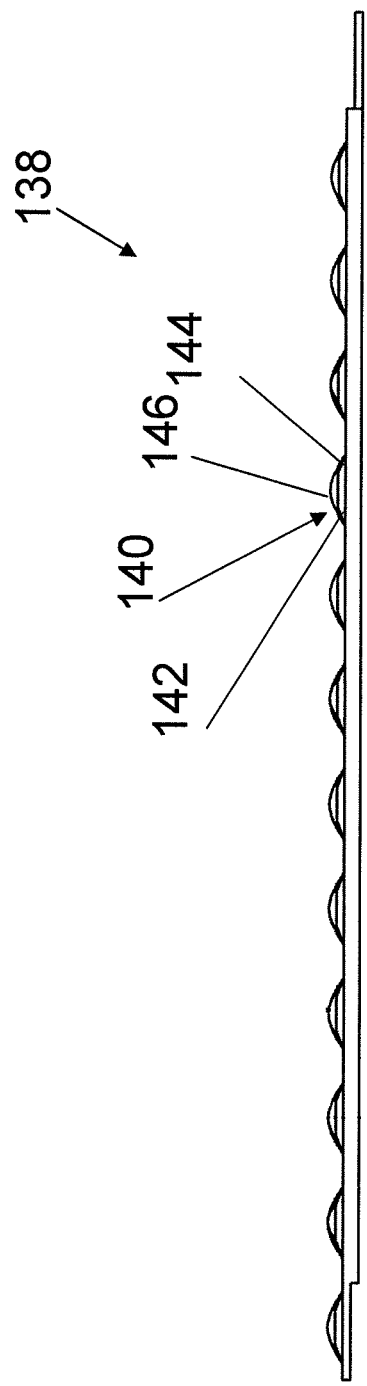
FIG. 19B is a side view of the alternative embodiment of FIG. 19A.

FIGS. 19A-B illustrate an alternative embodiment illustrating an alternative mat 138 with projections 140 having a square base section 142 with sides 44 that rise upward to blend with a semi-circular top section 146.

Figure 6:
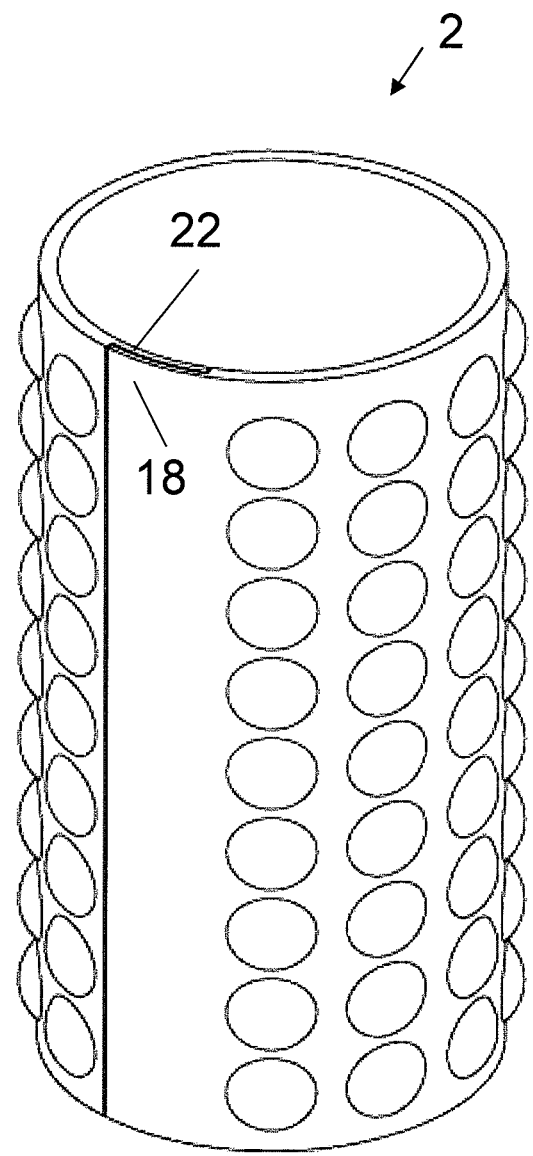
FIG. 6 is a perspective view of the roller flat mat of FIG. 5 rotated in a counter-clockwise position.

FIG. 6 is a perspective view of the flat mat 2 in a rolled configuration as illustrated in FIG. 5 rotated in a counter-clockwise position.

Figure 7:
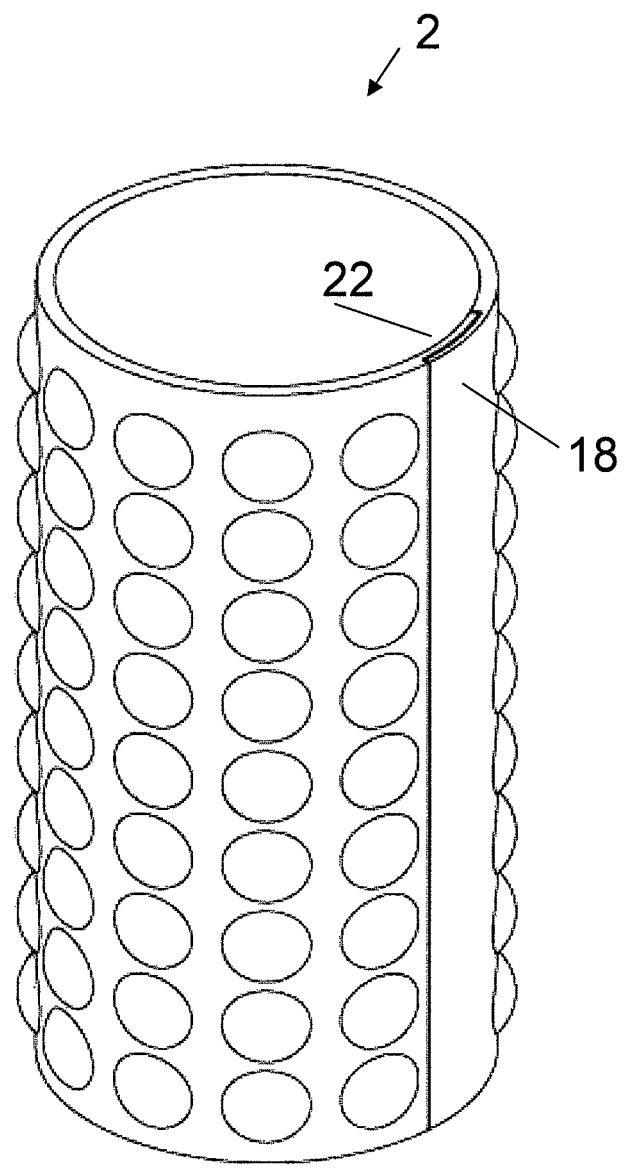
FIG. 7 is a perspective view of the roller flat mat of FIG. 5 rotated in a clockwise position.

FIG. 7 is a perspective view of the flat mat 2 in a rolled configuration as illustrated in FIG. 5 rotated in a clockwise position.

Figure 8:
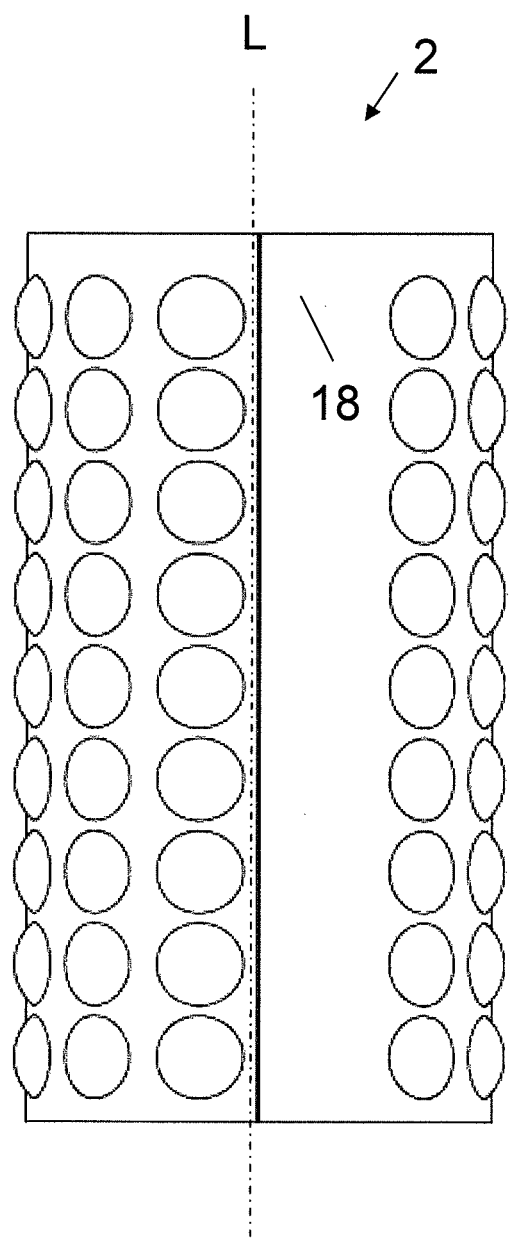
FIG. 8 is a side view of the roller flat mat of FIG. 5.

FIG. 8 is a side view of the flat mat 2 in a rolled configuration as illustrated in FIG. 5 showing longitudinal axis L that forms the center axis of the rolled cylinder.

Figure 9:
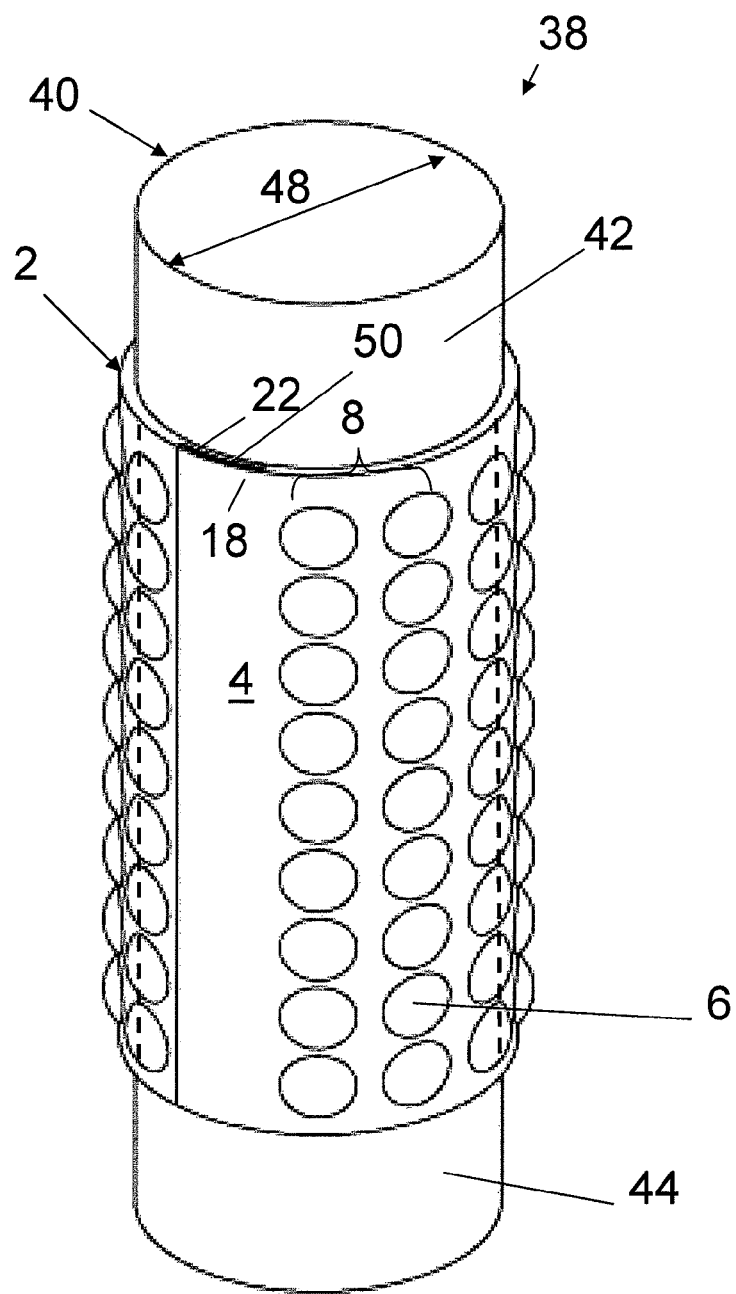
FIG. 9 is a perspective view of another embodiment of the present invention for an exercise roller, which has an outer surface with a plurality semi-circular projections arranged in rows and an insert therein having opposing ends without semi-circular projections.
Figure 10:
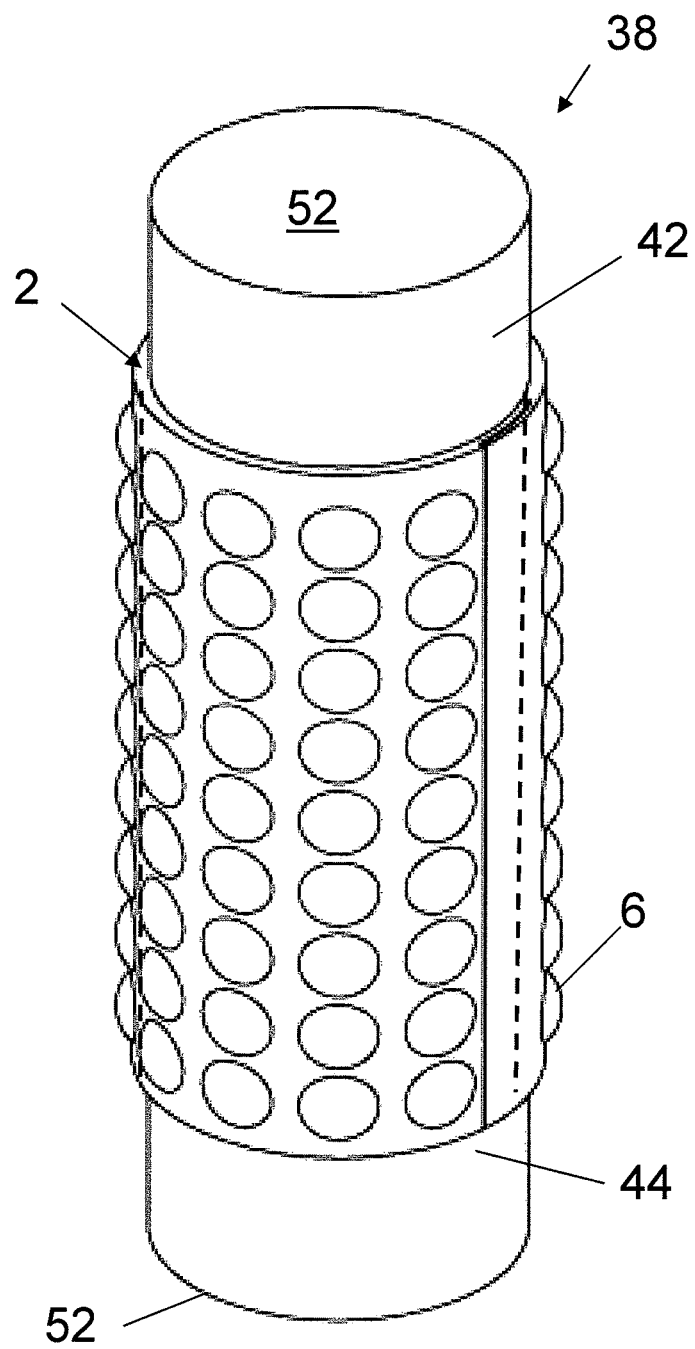
FIG. 10 is a perspective view of the exercise roller of FIG. 9 rotated counter-clockwise.
Figure 11:
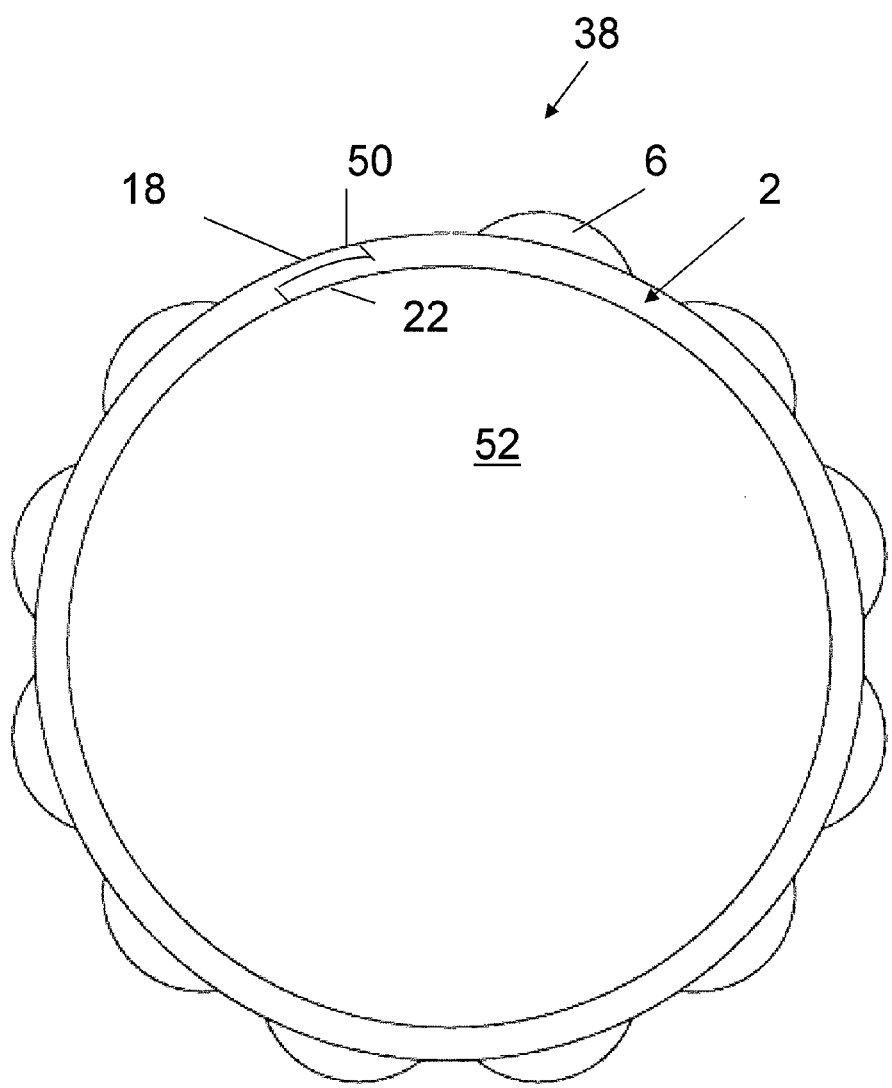
FIG. 11 is an end view of the exercise roller of FIG. 9.
Figure 12:
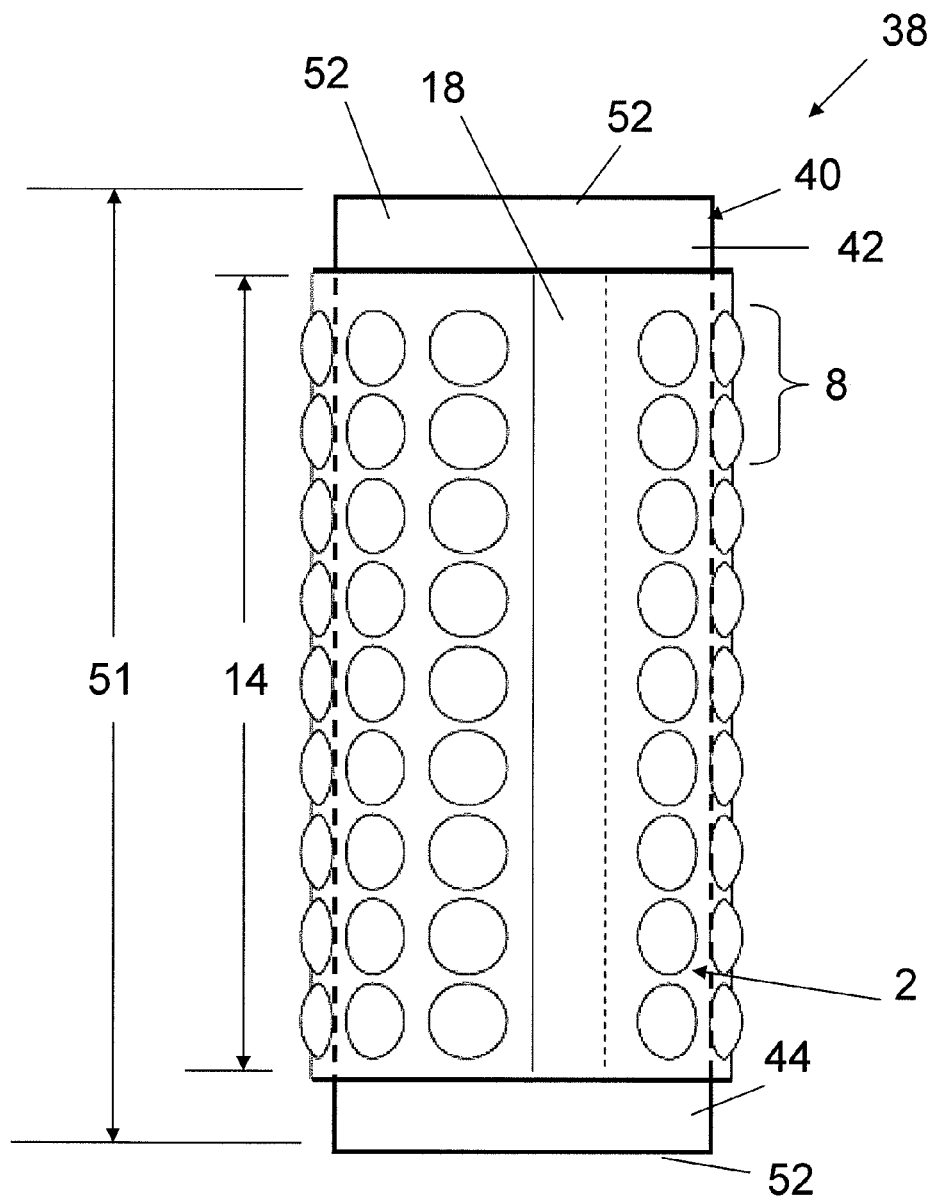
FIG. 12 is a side view of the exercise roller of FIG. 9.

Another embodiment of the present invention is an exercise roller 38 illustrated in FIGS. 9-12 showing flat mat 2 wrapped around an insert 40 connecting at overlapping end section 50 of ends 18, 22. FIG. 9 is a perspective view of embodiment 38 of the present invention, which has an top or outer surface 4 with a plurality semi-circular projections 6 arranged in rows 8 and an insert 40 therein having opposing ends 42, 44 without semi-circular projections 6. FIG. 10 is a perspective view of exercise roller 38 of FIG. 9 rotated counter-clockwise. FIG. 11 is an end view of exercise roller 38 of FIG. 9 showing end surface 52. FIG. 12 is a side view of exercise roller 38 of FIG. 9 illustrating length 51 of insert 40 relative to width 14 of flat mat 2. Insert 40 can be constructed of foam or styro-foam. Diameter 48 of insert 40 is substantially equivalent to length 46 of semi-circular projection portion of flat mat 2 (see FIG. 1) plus overlapping end section 50, which is the longer of either top surface cutout length 24 or bottom surface cutout length 28. Length 51 of insert 40 can be substantially equal to or greater than width 14 of flat mat 2. FIG. 12 illustrates length 51 being greater than width 14. The embodiment where length 51 equals width 14, which effectively eliminates opposing ends 42, 44 without semi-circular projections 6, such that ends 52 are substantially adjacent to semi-circular projections 6.

Figures 13, 14:
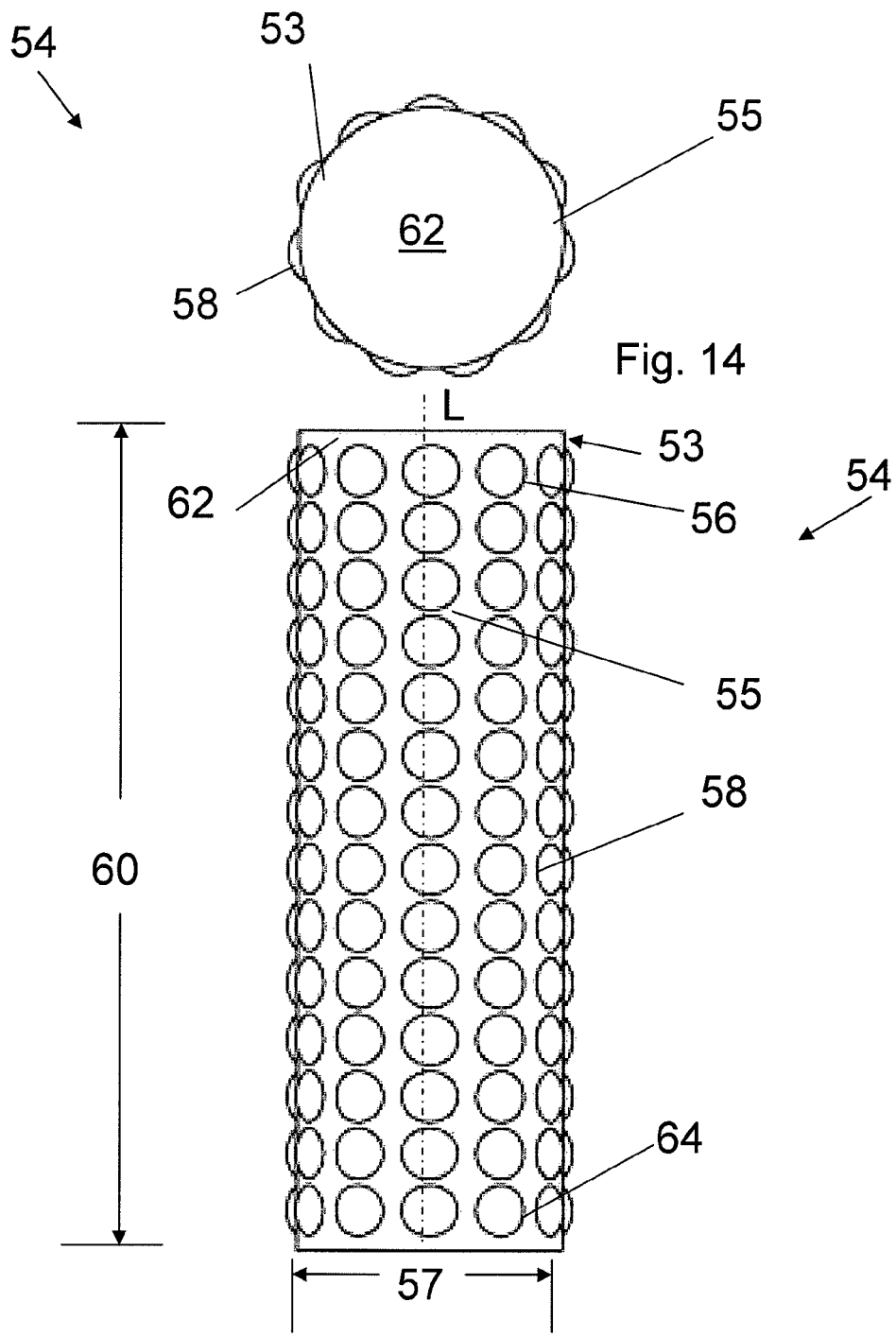
FIG. 13 is a side view of another embodiment of the present invention for an exercise roller, which has an outer surface with a plurality of semi-circular projections arranged in rows and an insert therein having semi-circular projections in proximity of the outer edges of the present invention.
FIG. 14 is an end view of the exercise roller of FIG. 13.

Yet another embodiment of the present invention is a monolithic exercise roller 54 without a diameter through a longitudinal axis L of the product illustrated in FIGS. 13-14 showing a cylinder 53 having diameter 57 that can be constructed of foam, styro-foam, TPE, SEBS, PU and Urethane Gels, as well as silicone materials, with Colloidal Silver additives suspended therein. Outer surface 56 of cylinder 53 has raised geometry 58 that traverses the entire circumference surface 55 in various dimensional shapes and designs including but not limited to raised semi-circular bumps or projections as shown in FIGS. 13-14 in close proximity of and adjacent to the outer edges 62, 64. This monolithic structure eliminates the need to wrap a substrate with the Colloidal Silver suspended therein around the perimeter of the cylinder.

Yet another embodiment of the present invention is a monolithic exercise roller 54 illustrated in FIGS. 13-14 showing a cylinder 53 having diameter 57 that can be constructed of foam, styro-foam, TPE, SEBS, PU and Urethane Gels, as well as silicone materials, with Colloidal Silver additives suspended therein. Outer surface 56 of cylinder 53 has raised geometry 58 that traverses the entire circumference 55 in various dimensional shapes and designs including but not limited to raised semi-circular bumps or projections as shown in FIGS. 13-14 in close proximity of and adjacent to the outer edges 62, 64. This monolithic structure eliminates the need to wrap a substrate with the Colloidal Silver suspended therein around the perimeter of the cylinder.

Examples of flat mat 2 can have total lengths defined as the sum of top surface cutout length 24, bottom surface cutout length 28, and semi-circular projection portion length 46 about 18 inches to about 26 inches. Flat mat 2 can have widths about 14 inches to about 40 inches. However, lengths and widths longer or shorter are acceptable.

Examples of the exercise rollers 38, 54 can have lengths about 14 inches to about 40 inches and diameters about 6 inches to about 8 inches. However, lengths longer or shorter and diameters larger or smaller are acceptable.

Figure 16A:
FIG. 16A is a side view of the present invention in the form of a flat mat without a plurality of semi-circular projections arranged in rows.
Figure 16B:
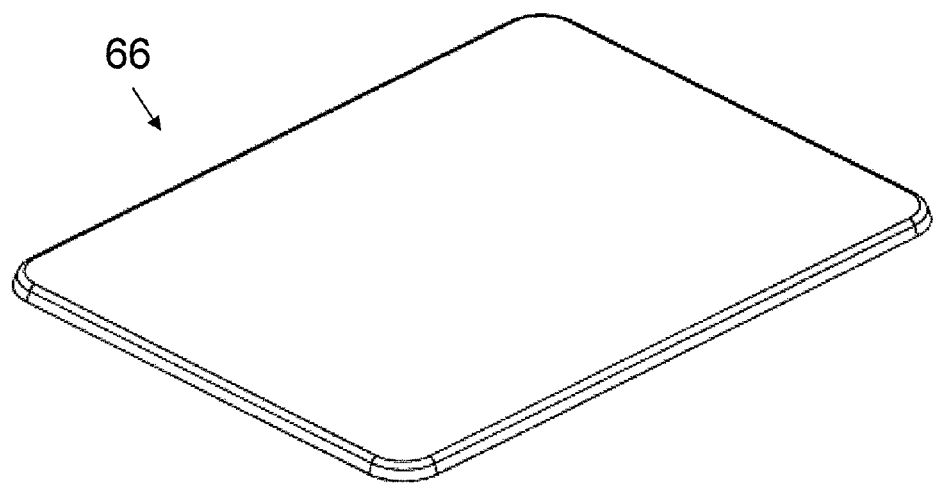
FIG. 16B is a perspective view of the flat mat of FIG. 16A.

FIG. 16A is a side view of the present invention in the form of a flat mat 66 without a plurality of semi-circular projections arranged in rows. FIG. 16B is a perspective view of the flat mat 66.

Figure 17A:
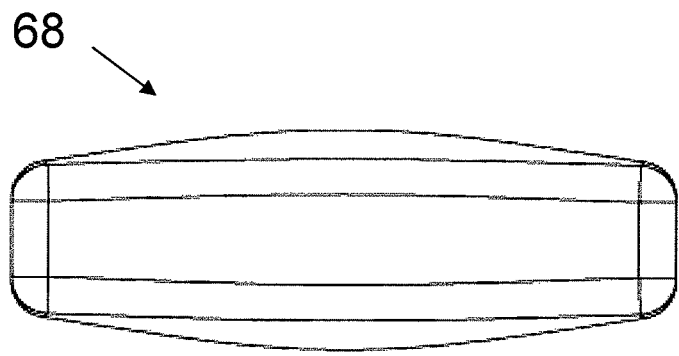
FIG. 17A is a side view of the flat mat in the form of a block without a plurality of semi-circular projections arranged in rows.
Figure 17B:
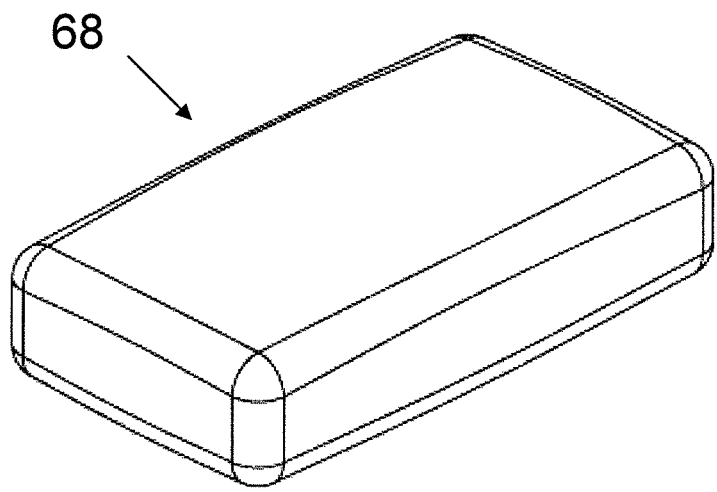
FIG. 17B is a perspective view of the block of FIG. 17A.

FIG. 17A is a side view of the present invention in the form of a block 68 without a plurality of semi-circular projections arranged in rows. FIG. 17B is a perspective view of the block 68. An alternative embodiment (not shown) of block 68 can include a plurality of semi-circular projections arranged in rows.

Figure 18:
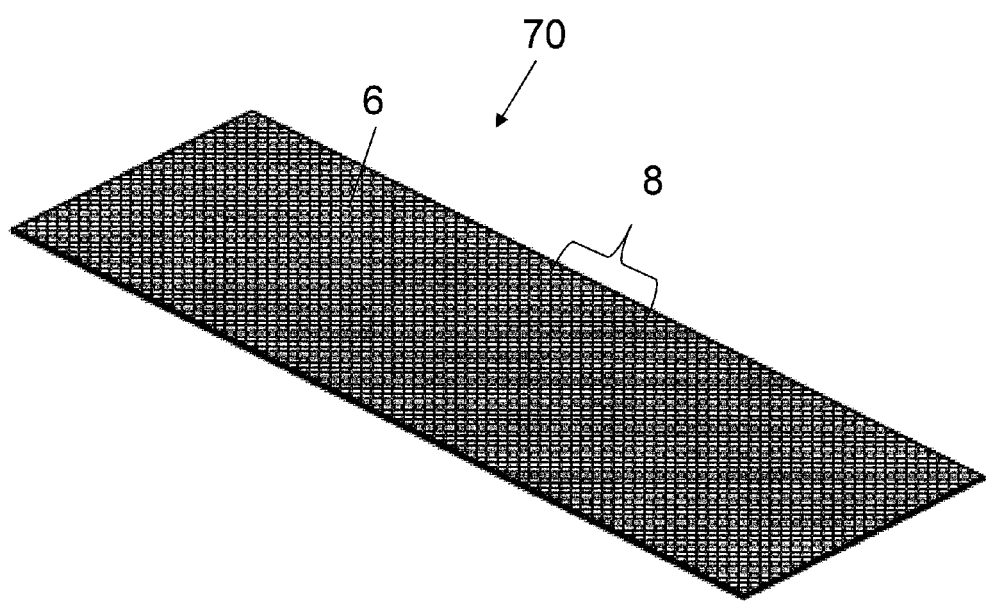
FIG. 18 is a perspective view of the present invention in the form of a Pilates mat with a plurality of semi-circular projections arranged in rows.

FIG. 18 is a perspective view of the present invention in the form of a Pilates mat 70 with a plurality of semi-circular projections 6 arranged in rows 8.

Yet another antimicrobial colloidal silver product according to the present invention is a shoe insert (not shown).

Figure 20:
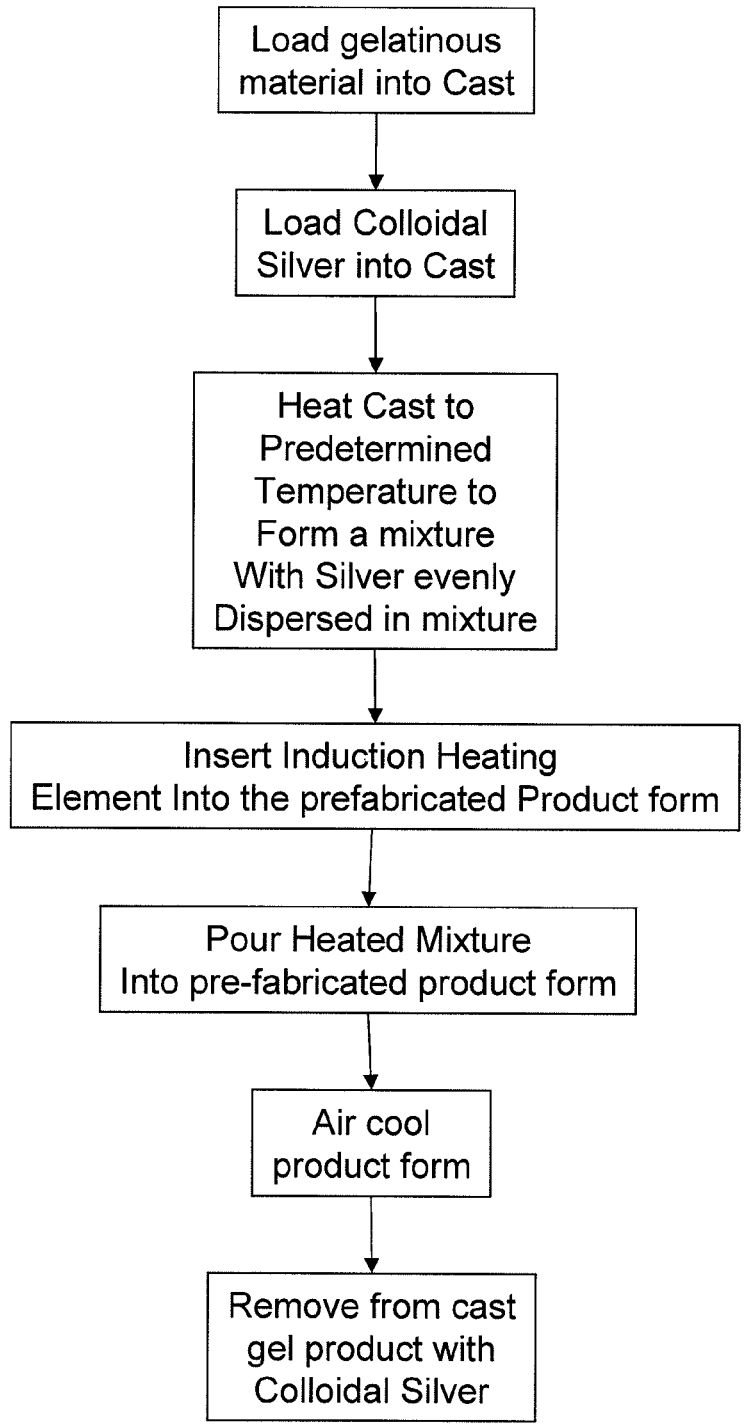
FIG. 20 is a flow diagram of the manufacturing process including the incorporation of the induction heating elements into the pre-fabricated form to embed the induction heating elements within the gel material of the formed product.
Figure 21:
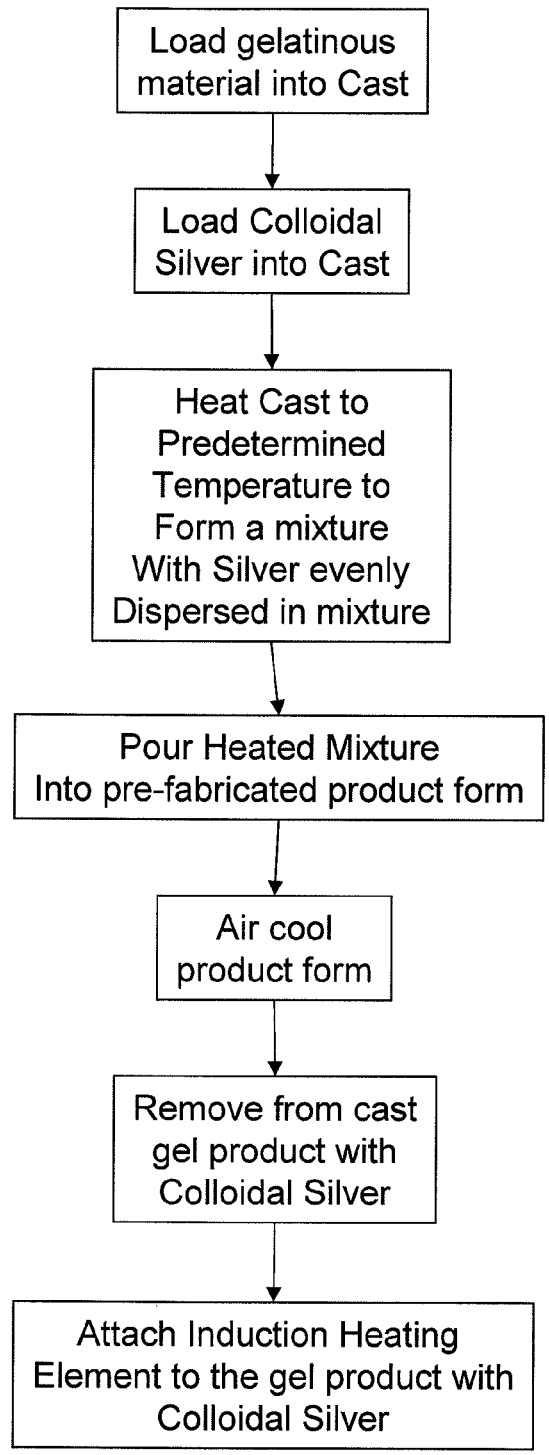
FIG. 21 is a flow diagram of the manufacturing process including the attachment of the induction heating elements to the gel material of the formed product.

Alternative embodiments of the present invention for all products can be capability of generating heating. The products can be microwaveable or include induction heating elements power by AC or DC sources. The induction heating elements can either be embedded within the gel material of the formed product (FIG. 20) or attached to an outer surface of the formed product (FIG. 21). The maximum temperature of the heating element is less than the boiling point of material, depending on the composition of the gel material.

Further alternative embodiments of the present invention for all products can be capable of being cooled to greater than the freezing point of the gel material such that the properties of malleability and cushioning are still present. The freezing point ranges depends on the composition of the gel material. The product can be place in the refrigerator or freezer to achieve the desired cooling temperature.

While the disclosure has been described in detail and with reference to specific embodiments thereof, it will be apparent to one skilled in the art that various changes and modifications can be made therein without departing from the spirit and scope of the embodiments. Thus, it is intended that the present disclosure cover the modifications and variations of this disclosure provided they come within the scope of the appended claims and their equivalents.

What is claimed is:

1. A product of the process comprising the steps of:
   loading a gelatinous material into a cast;
   loading Colloidal Silver into the cast;
   heating the cast to a predetermined temperature to form a mixture with Colloidal Silver evenly dispersed in mixture;
   pouring heated mixture into a prefabricated form that are in the shape of the products to be derived from the casting of the materials;
   air cooling the prefabricated form; and
   removing the gel product with Colloidal Silver from the prefabricated form, wherein the gelatinous material is a mixture of Substance A and Substance B at a ratio of A:B about 1:1, wherein Substance A is Polymeric Methylene diphenyl di-isocyanate (MDI) 100% and Substance B is 265 Molecular weight (Mw) polyether triol 100%; and
   wherein the product is a cylinder.

2. The product according to claim 1, wherein the cylinder has raised geometric projections on the surface of the cylinder.

* * * * *